United States Patent [19]

Chatterjee et al.

[11] Patent Number: 4,892,883

[45] Date of Patent: Jan. 9, 1990

[54] PHARMACEUTICAL COMPOSITIONS CONTAINING BILOBALIDE FOR THE TREATMENT OF NEUROPATHIES AI

[75] Inventors: Shyam S. Chatterjee; Benard L. Gabard, both of Karlsruhe; Hermann E. W. Jaggy, Bad Schonborn, all of Fed. Rep. of Germany

[73] Assignee: Willman - Schwabe GmbH & Co., Karlsruhe, Fed. Rep. of Germany

[21] Appl. No.: 256,233

[22] Filed: Oct. 11, 1988

Related U.S. Application Data

[63] Continuation of Ser. No. 134,577, Dec. 8, 1985, abandoned, which is a continuation-in-part of Ser. No. 802,539, Nov. 27, 1985, abandoned, which is a continuation of Ser. No. 662,598, Oct. 19, 1984, Pat. No. 4,571,407.

[30] Foreign Application Priority Data

Oct. 27, 1973 [DE] Fed. Rep. of Germany ....... 3338995

[51] Int. Cl.$^4$ .............................................. A61K 31/36
[52] U.S. Cl. ................................................... 514/464
[58] Field of Search ......................................... 514/464

Primary Examiner—Stanley J. Friedman
Attorney, Agent, or Firm—Kenyon & Kenyon

[57] ABSTRACT

Medicaments containing bilobalide which can be used to control nervous diseases are described.

7 Claims, 2 Drawing Sheets

PHARMACEUTICAL COMPOSITIONS CONTAINING BILOBALIDE FOR THE TREATMENT OF NEUROPATHIES AI

This application is a continuation of application Ser. No. 134,577, filed Dec. 8, 1985 now abandoned which is a continuation-in-part of U.S. application Ser. No. 802,539 abandoned, filed Nov. 27, 1985, which, in turn is a continuation of U.S. application Ser. No. 662,598, filed Oct. 19, 1984, now U.S. Pat. No. 4,571,407.

BACKGROUND OF THE INVENTION

Extracts prepared from Ginkgo biloba have been used in medicine since 1965 for the treatment of disturbances of cerebral and peripheral arterial blood flow; see German Pat. Nos. 17 67 098 and 21 17 429. These extracts are called monoextracts (see S. S. Chatterjee and G. Trunzler, Ärztezeitschrift für Naturheilverfahren 22 (1981), 593 to 604). They contain flavone glycosides as the main constituent.

The isolation of a lactone compound having the molecular formula $C_{15}H_{18}O_8$ from the leaves of Ginkgo biloba was first mentioned in 1967 by R. T. Major (Science 157 (1967), 1270 to 1273). The physicochemical properties of this compound and derivatives were described, and the name bilobalide was proposed, by K. Weinges and W. Bähr (Liebigs Ann. Chem. 724 (1969), 214 to 216). The following structural formula I was proposed for bilobalide in a combined publication by the groups of K. Nakanishi et al., R. T. Major et al. and K. Weinges et al. (J. Amer. Chem. Soc. 93 (1971), 3544 to 3546)

No medicinal effects of bilobalide have been disclosed. However, it is known that bilobalide has no fungicidal action on Monilia fructicola and Penicillium glaucum nor any bactericidal action on Escherichia coli. Moreover, it is known that bilobalide has no inflammatory action on the mouse ear.

Investigations have shown that the known monoextracts only contain negligble amounts of bilobalide.

Clinical investigations have now surprisingly shown that the Ginkgo biloba extract substance bilobalide has favourable effects on existent neuropathies, neurological and mental functions. It was furthermore shown that monoextracts which were prepared in such a manner that they retain the natural content of bilobalide of Ginkgo biloba or to which bilobalide is added show in addition to the therapy of disturbances of blood flow the above mentioned favourable effects on existent neuropathies, neurological and mental functions. To date, these actions have been attributed exclusively to the demonstrated actions of the monoextract in promoting blood flow. However, pharmacological investiations have shown that the bilobalide-containing monoextracts possess additional properties which go beyond the promotion of blood flow, and which might be responsible for the improvements in nervous diseases observed clinically.

SUMMARY OF THE INVENTION

The present invention is based on the surprising finding that bilobalide is suitable for the treatment of certain nervous diseases. Thus, the invention has the object of making available medicaments containing bilobalide for the treatment of nervous diseases. Furthermore it was surprisingly shown that bilobalide-containing monoextracts have these beneficial effects to a higher degree than medicaments containing bilobalide as the only active ingredient. A further object ot the invention therefore is the provision of monoextracts of the leaves of Ginkgo biloba containing an effective amount of bilobalide.

BRIEF DESCRIPTION OF THE DRAWINGS

This application contains two drawings, wherein.

DETAILED DESCRIPTION OF THE INVENTION

The disorders which can be treated with bilobalide or medicaments containing bilobalide are termed neuropathies, encephalopathies and myelopathies and are associated with at least one of the following symptoms: paraesthesia, paresis, abnormal reflexes, muscular atrophy, muscle spasms, tremor, disturbances of superficial and deep sensibility, headaches and pains in the limbs, disturbances of speech, vision and hearing, vertigo, disturbances of consciousness, lack of coordination and concentration, memory impairment and disorientation. The bilobalide-containing medicaments are suitable for the treatment of neurological disorders which are caused by or associated with pathological changes in the myelin layer of the nerve fibres.

The great importance of the integrity of the myelin for normal neurological function is generally known. It depends on normal functioning of Schwann's membrane in the peripheral nervous system and the oligodendrocytes in the central nervous system and is, moreover, only ensured when the neurons and axoms are intact. Damage to myelin is frequently the consequence of a large number of unconnected pathological states and it is induced by, for example, infections, intoxication, immunological disturbances, genetic defects, tumours, cerebral oedema, trauma and anoxia. Damage to myelin can occur directly or indirectly. Accordingly, a distinction is made between primary and secondary forms. The primary include inflammatory and immunological demyelinating diseases (e.g. multiple sclerosis, post-infectious encephalitis and the Guillain-Barré syndrome), metabolic neuropathies having genetic causes (e.g. the leukodystrophies, the Refsum syndrome and Pelizaeus-Merzbacher disease) and metabolic neuropathies due to toxic effects (e.g. diphtheritic polyneuritis and lead encephalitis). The secondary forms include traumatic neuropathies (e.g. Waller's degeneration), sclerosing neuropathies (e.g. sclerosing panencephalitis), the diabetic, alcohol-related, serogenetic, hereditary and vascular polyneuropathies, and the damage to myelin associated with hemiplegia following apoplexy.

The complex aetiology and pathogenesis of the nervous diseases make it difficult to select pharmacological models suitable for testing potentially effective substances. One possibility is that of testing the therapeutic action of these substances on animals which suffer from neurological signs. It is possible to induce morphological, pathological and electrophysiological signs, resembling the disease, in animals by neurotoxic poisons, such as, for example, organic tin compounds or hexachlorophene [2,2'-methylene-bis(3,4,6-trichlorophenol)]. It is known that, for example, triethyltin chloride brings about an increase in the water content in the brain of various species and induces specific myelopathy in the nerves, and these lead to neuropathies (Int. Rev. Neurobiol, 12 (1970), 45–86). In a similar manner, hexachlorophene produces oedematous damage in the brain of many species, including humans (Arch. Environ. Health, 23 (1971), 114–118; J. Pediatrics, 82 (1973), 976–981) associated with Losses and changes in myelin in the nerves (J. Lipid Res., 12 (1971), 570–579; Acta Neuropathol., 53 (1983) 65–74). For this reason, animals treated with this poison are particularly well suited as a model for the disorders mentioned above. Intoxication with triethyltin chloride has been used as a model for myelin damage (Neurochem., 21 (1973), 357–372) and as a model for degenerative disorders of neurological origin (Pharmacol. Biochem. Behavior, 5 (1976), 299–307).

The efficacy of bilobalide has been demonstrated in the following pharmacological models.

EXPERIMENT 1

Male Sprague-Dawley rats (200–300 g body weight) are offered an aqueous solution containing 0.002 per cent triethyltin chloride (abbreviated to TET) as drinking liquid for 14 days. Control animals received water. The Gingko biloba monoextract (EGB) with or without bilobalide and the various test substances are administered orally 1×daily throughout these 14 days. On day 15, the animals are sacrificed, the brain is removed and its water and electrolyte contents are determined. The body weight of the animals during the experiment is checked daily. Treatment with bilobalide and/or EGB containing bilobalide shows a good protective effect against the decrease in body weight and the increase in the water and Na+ contents in the brain. The results are summarised in Table I.

TABLE I

| Test substance | Dose | Drinking Liquid | Mean body weight (g) Initial | Mean body weight (g) 14 days | % water | Brain Na+ mmol/kg dry weight | Brain K+ mmol/kg dry weight | Na+/K+ |
|---|---|---|---|---|---|---|---|---|
| Water | | Water | 250 | 320 | 77.90 ± 0.07 | 193.6 ± 0.7 | 442.7 ± 3.9 | 0.44 ± 0.003 |
| Water | | TET 0.002% | 250 | 204 | 80.51 ± 0.19 | 284.4 ± 7.4 | 444.4 ± 3.7 | 0.64 ± 0.020 |
| EGB* | 100 mg/kg | TET 0.002% | 238 | 290 | 78.36 ± 0.16 | 189.9 ± 1.7 | 442.2 ± 3.0 | 0.43 ± 0.006 |
| EGB without flavones** | 60 mg/kg | TET 0.002% | 242 | 288 | 78.06 ± 0.15 | 186.7 ± 3.1 | 419.1 ± 2.9 | 0.44 ± 0.005 |
| Flavones from EGB | 40 mg/kg | TET 0.002% | 252 | 195 | 80.06 ± 0.27 | 241.3 ± 8.9 | 440.6 ± 3.0 | 0.55 ± 0.02 |
| Bilobalide | 20 mg/kg | TET 0.002% | 288 | 325 | 77.75 ± 0.11 | 187.9 ± 10.4 | 400.6 ± 5.3 | 0.45 ± 0.05 |
| | 10 mg/kg | TET 0.002% | 272 | 318 | 78.16 ± 0.09 | 198.3 ± 2.74 | 452.7 ± 12.9 | 0.44 ± 0.04 |
| | 5 mg/kg | TET 0.002% | 288 | 323 | 78.57 ± 0.19 | 162.6 ± 5.4 | 418.9 ± 14.4 | 0.39 ± 0.020 |
| EGB without flavones and without bilobalide | 60 mg/kg | TET 0.002% | 245 | 210 | 80.29 ± 0.11 | 297.8 ± 6.7 | 429.4 ± 3.3 | 0.69 ± 0.01 |

*containing bilobalide in a concentration of 3.38%
**containing bilobalide in a concentration of 6.1%

EXPERIMENT 2

In another experiment, male Sprague-Dawley rats (200–250 g body weight) receive intraperitoneal injections of 20 mg/kg hexachlorophene (suspended in 0.2% agar) for 2 days and only 10 mg/kg on the 3rd day. The test substances are administered orally after administration of hexachlorophene.

The control animals receive only 0.2% agar i.p. or tap water orally. On the 4th day, the animals are sacrificed and the water and electrolyte contents in the brain are determined. The body weight of the animals is measured daily throughout the 4 days. As the results in Table II show, treatment with bilobalide and/or EGB containing bilobalide protects the animals from the development of cerebral oedema and prevents the reduction in body weight.

EXPERIMENT 3

Figure 1:
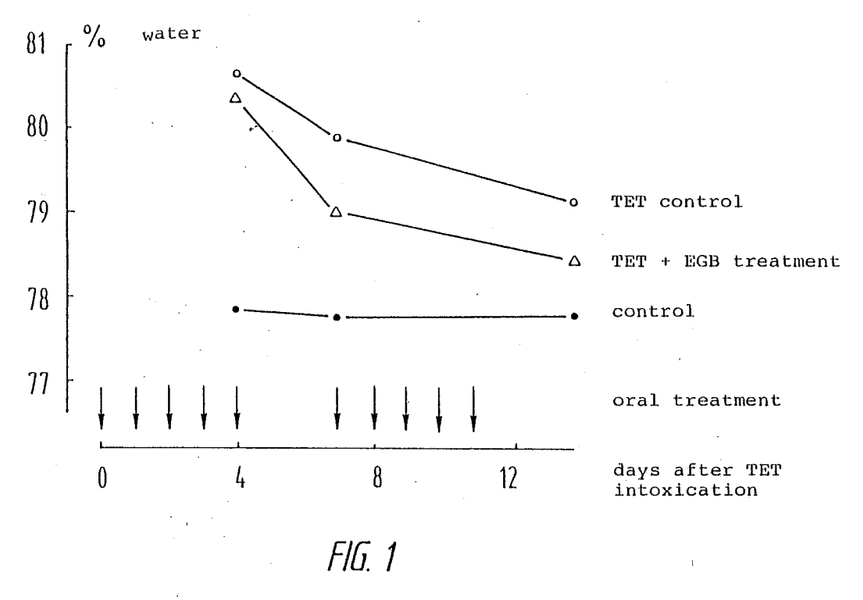
FIG. 1 is a graphic illustration of brain water content data generated in Experiments 1 to 3.
Figure 2:
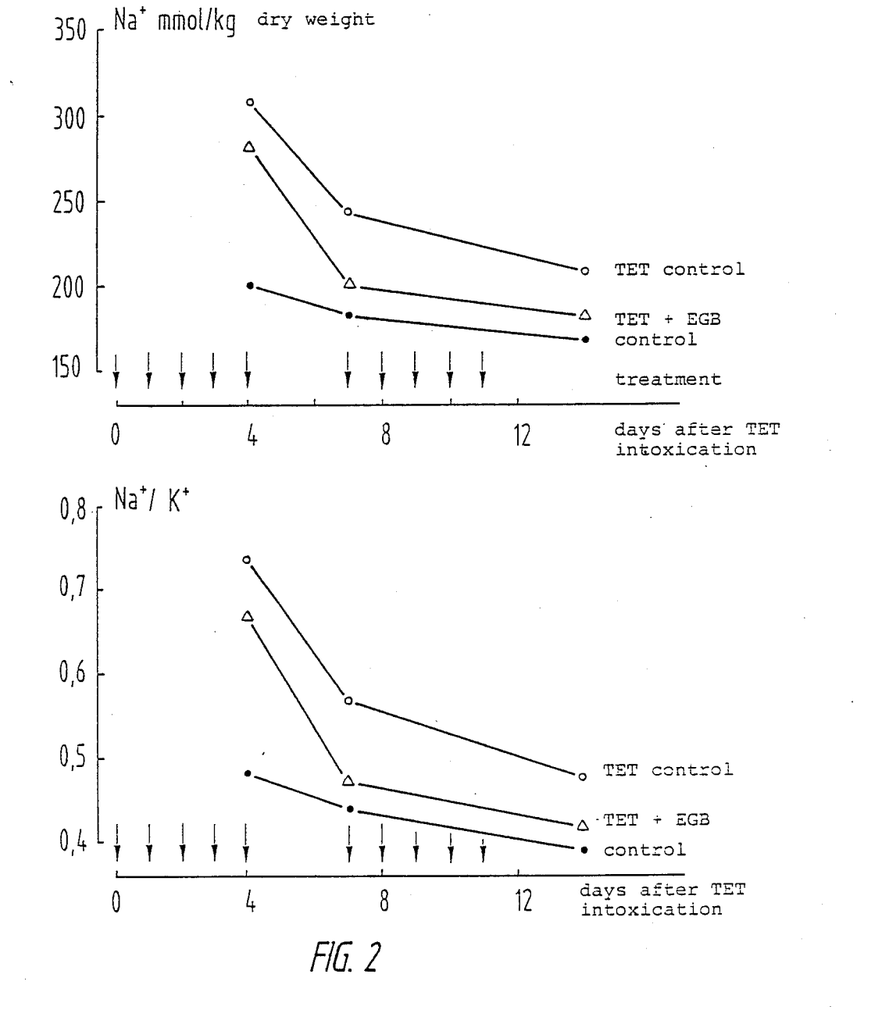
FIG. 2 is a graphic illustration of electrolyte sodium and sodium/potassium ratio data generated in Experiments 1 to 3.

The curative action of EGB containing bilobalide is demonstrated in a third experiment. As in Experiment 1, the animals are offered a 0.002 per cent triethyltin chloride solution as drinking liquid in place of drinking water for 14 days. The oral treatment with the test substances is started on the 15th day, 1×daily for 5 days a week, with simultaneous replacement of the TET solution by normal tap water. The water and electrolyte contents of the brain are measured at various times after withdrawal of the TET solution and after the start of the treatment. The treatment with EGB containing bilobalide brings about a more rapid return of the water and Na+ contents of the brain to normal values and thus shows that it has good curative action. The results of this experiment are presented in FIGS. 1 and 2.

EXPERIMENT 4

The investigations of the protective action against damage to myelin and its expression as neuropathy is likewise carried out on the triethyltin chloride model. When the animals are treated not for 14 days but for only 6 days with a 0.002 per cent TET solution administered in place of the drinking water, they show various signs of neuropathy although no cerebral oedema is detectable in this period. The neuropathy is quantified by measuring the consumption of food and water and by the changes in body weight. In addition, as a specific parameter, the pain reaction time in a hotplate test (at 50° C.) is measured (J. Pharm. Pharmacol., 9 (1957), 381). Oral treatment with bilobalide or EGB containing bilobalide carried out throughout these 6 days shows a good protective action against the neuropathic signs, as is clear from Table III.

ited by the known extracts containing practically no bilobalide or by the components of the Ginkgo biloba leaves.

TABLE II

| Test substance | Dose | Intraperitoneal treatment | Mean body weight (g) Initial | Mean body weight (g) 4th day | % water | Brain Na$^+$ mmol/kg dry weight | Brain K$^+$ mmol/kg dry weight | Na$^+$/K$^+$ |
|---|---|---|---|---|---|---|---|---|
| Water |  | 0.2% agar | 238 | 266 | 78.50 ± 0.14 | 207.6 ± 4.0 | 433.6 ± 4.1 | 0.48 ± 0.009 |
| Water |  | hexachlorophene | 237 | 228 | 80.01 ± 0.19 | 265.4 ± 2.6 | 423.6 ± 2.9 | 0.63 ± 0.02 |
| EGB* | 100 mg/kg | hexachlorophene | 245 | 253 | 79.10 ± 0.21 | 240.4 ± 10.9 | 432.3 ± 1.6 | 0.56 ± 0.02 |
|  | 50 mg/kg | hexachlorophene | 236 | 243 | 79.40 ± 0.17 | 240.7 ± 13.1 | 421.0 ± 2.6 | 0.57 ± 0.03 |
|  | 25 mg/kg | hexachlorophene | 230 | 236 | 79.86 ± 0.12 | 245.9 ± 11.3 | 417.8 ± 2.6 | 0.59 ± 0.02 |
| EGB without flavones** | 60 mg/kg | hexachlorophene | 242 | 252 | 78.74 ± 0.24 | 238.2 ± 12.8 | 437.9 ± 2.0 | 0.54 ± 0.03 |
|  | 30 mg/kg | hexachlorophene | 230 | 237 | 79.27 ± 0.09 | 227.7 ± 17.2 | 423.4 ± 4.0 | 0.54 ± 0.02 |
|  | 15 mg/kg | hexachlorophene | 239 | 240 | 79.55 ± 0.30 | 275.6 ± 10.3 | 422.6 ± 4.9 | 0.65 ± 0.02 |
| Bilobalide | 5 mg/kg | hexachlorophene | 264 | 270 | 77.93 ± 0.17 | 187.9 ± 4.0 | 414.5 ± 4.4 | 0.45 ± 0.01 |
| Flavones from EGB | 40 mg/kg | hexachlorophene | 250 | 240 | 80.51 ± 0.23 | 291.4 ± 20.0 | 432.7 ± 5.4 | 0.67 ± 0.04 |

*, ** same as in Table I

EXPERIMENT 5

In a similar manner, the curative action of bilobalid or extract containing bilobalide is investigated. The animals are offered a 0.002 per cent TET solution in place of drinking water for 6 days. Subsequently (from the 7th day), the TET solution is replaced by tap water and, simultaneously, the daily oral treatment is started. Treatment is continued for 6 days. The measured parameters (body weight, consumption of food and water, hotplate reaction time) are determined on the 6th day before the treatment and on the 14th day after the treatment. The results are summarised in Table IV.

The fact that treatment with EGB containing bilobalide or with bilobalide prevents the occurrence of neurotoxic signs and/of cerebral oedema, and that pre-existent damage can be made to regress more quickly, show that this treatment can eliminate damage to myelin and the signs resulting therefrom.

Bilobalide and monoextracts containing bilobalide have a stimulating effect on the cholinergic mechanisms of the central nervous system, which effect is not exhibited by the known extracts containing practically no bilobalide or by the components of the Ginkgo biloba leaves.

Said effect of the drug Ginkgo biloba is not only an extension of the known multifactor profile of efficacy, but may also be an extension of the range of indications of this drug. As is generally known, some degenerative disorders of neurological origin such as senile dementia or Alzheimer's disease are accompanied or caused by a decreased cerebral blood supply. These diseases cannot, however, efficiently be treated only with medicaments stimulating the blood flow or medicaments having an anti-ischemic action.

TABLE III

| Test substance | Dose | Drinking Liquid* | Mean body weight (g) Initial | Mean body weight (g) Final | Food consumption (g/animal/day) Initial | Food consumption (g/animal/day) Final | Water consumption (ml/animal/day) Initial | Water consumption (ml/animal/day) Final | Hotplate reaction time (sec) Initial | Hotplate reaction time (sec) Final |
|---|---|---|---|---|---|---|---|---|---|---|
| Water |  | Water | 245 | 280 | 25.6 | 24.4 | 37.0 | 33.2 | 39.4 ± 3.4 | 18.6 ± 2.1 |
| Water |  | TET 0.002% | 240 | 226 | 24.0 | 12.4 | 34.4 | 11.9 | 36.6 ± 4.3 | >60 |
| EGB* | 100 mg/kg/day | TET 0.002% | 245 | 257 | 25.9 | 20.2 | 37.2 | 20.7 | 36.9 ± 2.0 | 21.5 ± 3.32 |
| Bilobalide | 10 mg/kg/day | TET 0.002% | 241 | 261 | 24.3 | 22.1 | 35.1 | 21.9 | 28.9 ± 8.3 | 17.9 ± 5.54 |

*same as in Table I

TABLE IV

| Treatment | Dose | Body weight (g) After intoxication | Body weight (g) After treatment | Food consumption (g/animal/day) After intoxication | Food consumption (g/animal/day) After treatment | Water Consumption (ml/animal/day) After intoxication | Water Consumption (ml/animal/day) After treatment | Hotplate reaction time (sec) After intoxication | Hotplate reaction time (sec) After treatment |
|---|---|---|---|---|---|---|---|---|---|
| Water |  | 229 | 222 | 10.7 | 18.3 | 11.1 | 13 | 88.4 ± 4.7 | >90 |
| EGB* | 100 mg/kg | 212 | 260 | 11.4 | 19.7 | 10.8 | 21.7 | 84.4 ± 13 | 32.9 ± 14.9 |
| EGB* | 50 mg/kg | 229 | 246 | 14.9 | 18.6 | 11.6 | 22.4 | 82.1 ± 15.5 | 48.2 ± 22.3 |
| Bilobalide | 10 mg/kg | 227 | 232 | 8.9 | 18.6 | 12.7 | 23.1 | 87.36 ± 7.46 | 48.58 ± 18.44 |
| Bilobalide | 5 mg/kg | 236 | 242 | 10.4 | 17.4 | 11.4 | 31.4 | 88.1 ± 5.67 | 61.58 ± 21.86 |

*same as in Table I

Recent findings in the pathology of these diseases indicate that the synthesis or release of the neurohormonal acetylcholines in various areas of the brain is reduced as a consequence of decreased cerebral blood supply, hypoxia or other pathological changes. This again leads to a reduction of the cholinergic activities of the central nervous system, thus provoking the pathological symptoms. The treatment of patients showing said symptoms with substances similar to Physostigmine which stimulate the cholinergic system of the central nervous system by inhibiting the decomposition of acetylcholine, improves the patients' condition (Price D. L.; Struble R. G.; Whitehouse P. J.; Cork L. C.; *Drug Development Research,* 5, 59–68, 1985; Davis P.; *Drug Development Research,* 5, 69–76; 1985 and Johns C. A.; Haroutunian V.; Greenwald B. S.; Mohs R. C.; Davis B. M.; Kanof P.; Horvath T. B.; Davisk L.; *Drug Development Research,* 5, 77–96, 1985). All these findings confirm that diseases caused or accompanied by ischemia are of complex pathogenesis and that prevention and treatment of such diseases are only possible when using multifactor medicaments.

Sofar, the use of extracts from Ginkgo biloba leaves or their components for treating dementia or Alzheimer's disease has not been known. This is most probably due to the fact that the presently known and applied extracts do not contain the active ingredients necessary for this therapy and that the stimulating effects of the drug on the cholinergic system have not been known.

This disadvantage can be overcome by selectively adding bilobalide to the known monoextracts in an amount resulting in a concentration of about 0.5% to about 40%, prefably about 3% to about 20%. Such "enriched" extracts have the following properties:

(1) all pharmacological activities of the drug Ginkgo biloba, that have been found useful sofar, (2) the potency of a known active ingredient of the drug, namely bilobalide is higher in the extract than the potency of the isolated pure substance, (3) stimulating effect on the cholinergic system of the central nervous system.

It therefore can be said that this extract will be more effective in the therapy of diseases caused by defective circulation (and malnutrition) than all the hitherto known extracts from Ginkgo biloba leaves and that, additionally, this extract is useful in the therapy of dementia or Alzheimer's disease. This "enriched" extract is also suitable as an additional therapeutic medicament together with the known cholinomimetics for treating various diseases characterized by myasthenia and rapid tiring (e.g. Myasthenia Gravis or other kinds of paralysis of the skeletal muscles). This report summarizes the results of the pharmacological experiments carried out sofar which support the above statements.

IMPORTANT MATERIALS USED

Table V gives a brief definition of the "enriched" extract employed in the experiments.

NMRI-mice, Sprague-Dawley rats and rabbits and guinea-pigs of mixed breed were subjected to the experiments.

TOXICITY AND LIMIT OF TOLERANCE

In pilot tests, the acute limits of tolerance of the "enriched" extract were examined after intravenous (i.v.), oral (p.o.) and intraperitoneal (i.p.) administration in a high dose range. Groups of 5 male and 5 female mice (body weight between 20 and 25 g) were treated with the extract (200 mg/kg i.v.; 1 g/kg i.p.; 2 g/kg p.o., respectively). During the following 5 days the symptoms of toxicity and the death rates were observed. The results of the experiment are shown in Table VI.

In view of the high dose administered and of the low death rates and further toxicity symptoms it can be concluded that the examined extract is not toxic.

TABLE V

| Analysis of the "enriched" extract from Ginkgo biloba | |
|---|---|
| Component | Amount, % |
| Flavone glycosides | 24.10 |
| Bilobalide | 3.38 |

TABLE VI

| Pilot toxicity tests of the bilobalide-containing extract from Ginkgo biloba % deaths (other changes observed) after | | |
|---|---|---|
| i.v. administration (200 mg/kg) in aqueous solution pH = 1.4 | i.p. administration (1 g/kg) | p.o. administration (2 g/kg) |
| 0 (no changes) | 0 (pain reaction signs at the site of injection) | 0 (sedative effect) |

VASCULAR AND CARDIAL EFFECTS

The favourable cardial and blood circulation stimulating side effects of various concentrations of the extract were compared at the isolated, perfused heart of a guinea-pig (Langendorff heart), applying the method described by Bünger et al (Pflügers Arch. 353, 317–326, 1975). The following parameters were determined: coronary flow, contractility and pulse rate of the heart. After a stabilization period of 30 min an increased dose of the extract was added to the perfused heart and the influence of the various extract concentrations on the measurement parameters was registered. 5 different heart preparations were used.

The results obtained are shown in Table VII. It was found that the coronary flow improving effect of the extract depends on the dose contained therein.

The "enriched" extract hardly influences the heart rate and has only an insignificant reducing effect on the contractility. The extract has a favourable pharmacological profile of efficacy for the therapeutic utilization of the drug Ginkgo biloba.

ANTI-HYPOXIC EFFECT

The protective actions of the extract against hypoxia were compared in a Hypobare-Hypoxia model, according to a method described by Nakanishi et al (Life Sci 13, 467–478, 1973). 4 mice (2 control animals and 2 treated animals) were put into a vacuum desiccator (3.51). A negative pressure of 170 mmHg was generated therein within 20 sec. The survival times of the animals under these hypoxia conditions were determined. The test substance was administered intraperitoneally in an aqueous solution 30 min before the experiment began. The control animals were only treated with solvents. The maximum observation period of the survival times was 8 min. The survival time of the treated animals tolerating the hypoxia condition longer than this period was assumed to be 480 sec. None of the control animals survived longer than 180 sec. The percentage of the treated animals surviving longer than 3 min was defined as %-effect of the extract.

TABLE VII

Influence of the bilobalide-containing extract from Ginkgo biloba on the hearts of guinea-pigs (Langendorff heart)
The following values show maximum changes in percentage (M ± SEM) vis-a-vis the first run

| Concentration (µg/ml) | Contractility | Flow | Heart rate |
|---|---|---|---|
| 5 | 1.7 ± 0.74 | −4.2 ± 1.56 | 0.7 ± 0.50 |
| 10 | 0.8 ± 0.70 | 20.9 ± 4.82 | 1.1 ± 0.38 |
| 20 | −3.3 ± 1.93 | 90.5 ± 10.95 | 2.7 ± 1.49 |
| 40 | −10.3 ± 1.45 | 97.8 ± 22.63 | 8.0 ± 2.99 |

TABLE VIII

Influence of bilobalide-containing extract from Ginkgo biloba on the survival times of the mice in the Hypobare-Hypoxia model

| Dose (mg/kg) | number of animals/ group | Survival time in sec (M ± SEM) treated animals | Survival time in sec (M ± SEM) control animals | % effect |
|---|---|---|---|---|
| 100 | 14 | 188.6 ± 112.89 | 93.6 ± 22.08 | 50 |
| 200 | 8 | 410.0 ± 131.70 | 103.8 ± 38.70 | 87 |

The results obtained are shown in Table VIII. The anti-hypoxic effect of the tested extract was found to depend on the dose.

INHIBITION OF THROMBOCYTE AGGREGATION

The inhibiting effect on thrombocyte aggregation of the extract was examined in an in vitro test. The aggregation was measured in an optical aggregometer (chronometer) according to Born (Nature; London; 194, 927, 1962). Platelet-rich plasma (PRP) was obtained by centrifugation from the citrated blood of the rabbits (180 g) over a period of 15 min and aggregation was produced by the platelet-activating-factor (PAF-sigma). The test extract was dissolved in (physiological) saline (pH -7.4) and added in small quantities (10 l/ml) to the PRP. Five minutes after administering the substance and adding the physiological saline, respectively, the aggregation induced by the PAF was measured. The concentraction of PAF in the PRP was 0.4 ng/ml.

The extract showed a dependency of the inhibitory activity on the dose.

The dose ranges in which the extract inhibits thrombocyte aggregation and lowers the resistance of the vessels in the Langendorff heart test (see above) are very similar.

The inhibition of thrombocyte aggregation is a necessary and essential component of the mechanisms facilitating a therapy of ischemic diseases. In this respect, our test results clearly show that the "enriched" extract is extraordinarily suitable for the treatment of such diseases and that this extract has important advantages vis-à-vis other, hitherto known extracts.

RADICAL-TRAPPING PROPERTIES

A favourable biochemical mechanism of action of the drug Ginkgo biloba is that, due to the radical-trapping properties of its active ingredients, it prompts protective actions against membrane lesions and the accompanying pathological processes and activates other useful curing mechanisms. Therefore, these properties of the extract were compared in two experimental arrangements (in vivo and in vitro). The purpose of the in vivo tests was to examine the protective actions of the extract against diabetes induced by alloxan (an example for radical-induced pathological processes). The test animals used were male mice (body weight between 22 and 28 g) which were treated intraperitoneally with the test extract 30 min before administration of alloxan (sigma) (70 mg/kg i.v.). The control animals were treated with saline and the above dose of alloxan. The blood glucose level of the animals was determined 48 hours after administration of alloxan by a GOD method (Boehringer Kit). For a comparison, an untreated control group was also tested in each test series. These control animals were neither treated with alloxan nor with the test substance.

The test results given in Table IX illustrate that the tested extract has radical-trapping properties.

The results of the in vitro tests confirm this statement. In these tests, the influence of the extract on lipid peroxidation (a radical-induced reaction) of the cerebral homogenates of rats was examined according to the method published by our firm (Chatterjee S. S. and Gabard B.; 8th Intern. Cong. Pharmacology, Tokyo, Abstr. Page 483).

STIMULATION OF THE CHOLINERGIC SYSTEM

The stimulating effects of the extract on the cholinergic system of the central nervous system were determined in various experiments. In one of these experiments the influence of the extract on the spontaneous climbing behaviour (SCB) was examined according to the method described by Marcais et al. (*Psychopharmacology;* 56, 233–234, 1978). The results of these tests given in Table X show that the extract (similar to Physostigmine and other cholinomimetics) reduces the SCB of mice. The activity of the extract and of Physostigmine was inhibited only by specific anti-cholinergic agents entering the brain, such as Scopolamine and not influenced by antagonists to other receptors.

TABLE IX

Protective actions of the bilobalide-containing extract from Ginkgo biloba against alloxan-induced diabetes with mice

| Group | Extract dose (mg/kg) | Blood glucose values (mg/100 ml) 48 h after administration of alloxan (M ± SD) | % effect Ⓐ |
|---|---|---|---|
| untreated control | — | 136.4 ± 4.77 | — |
| alloxan control | — | 422.7 ± 15.62 | 0 |
| extract + alloxan | 50 | 197.9 ± 25.90 | 60 |
|  | 100 | 141.6 ± 4.59 | 100 |
|  | 200 | 155.1 ± 1.56 | 100 |

Ⓐ % of the treated animals whose blood glucose values were less than 250 mg/ml.

TABLE X

Influence of the bilobalide-containing extract from Ginkgo biloba and of other treatments on the spontaneous climbing behaviour (SCB) of mice

| Test No. | Treatment* | Dose (mg/kg) | Mean climbing score, animal (M ± SD) |
|---|---|---|---|
| I | none (control) | — | 6.88 ± 2.42 |
|  | extract | 200 (p.o.) | 2.63 ± 1.06 |
| II | none (control) | — | 6.75 ± 1.91 |
|  | Physostigmin | 0.10 (s.c.) | 1.39 ± 0.92 |
|  | Scopolamine | 0.25 (i.p.) | 6.63 ± 1.42 |
|  | Physostigmine + Scopolamine extract | 0.1 (s.c.) + 0.25 (i.p.) 200 (p.o.) | 6.38 ± 1.85 |

TABLE X-continued
Influence of the bilobalide-containing extract from Ginkgo biloba and of other treatments on the spontaneous climbing behaviour (SCB) of mice

| Test No. | Treatment* | Dose (mg/kg) | Mean climbing score, animal (M ± SD) |
|---|---|---|---|
| | + | + | 7.0 ± 2.14 |
| | Scopolamine | 0.25 (i.p.) | |
| | extract | 200 (p.o.) | 2.46 ± 0.82 |
| III | none (control) | — | 7.0 ± 1.51 |
| | Physostigmine | 0.025 (s.c.) | 5.75 ± 1.28 |
| | Physostigmine | 0.05 (s.c.) | 3.88 ± 2.23 |
| | extract | 50 (p.o.) | 6.88 ± 0.83 |
| | extract + Physostigmine | 50 + 0.025 | 2.83 ± 0.48 |
| | extract + Physostigmine | 50 (p.o.) + 0.05 (s.c.) | 0.86 ± 0.62 |

*The substances were applied 20 min before the observation period (30 min). In the combination experiments, the second substance was administered 5 min before the first substance. In further tests it could be shown that Sulpiride (Dopamine antagonist) and Naloxone (Morphine antagonist) do not influence the effects of Physostigmine and the extract, and that the extract does not potentiate the effects of Apomorphine (Dopamine antagonist) and Morphine.

Furthermore a very small dose of the extract potentiated the effects of Physostigmine. These findings prove that the drug Ginkgo biloba contains an active ingredient stimulating the cholinergic system, thus inducing changes in the behaviour of animals. The "enriched" extract comprises this component stimulating the cholinergic system, whereas these effects are not found with the extracts known sofar.

The anti-hypoxic effects of the cholinomimetics Pilocarpine and the acetylcholine-esterase inhibitor Physostigmine entering the brain are known. Pretreating the animals with small doses of the extract which show no anti-hypoxic effect potentiates the anti-hypoxic effects of Pilocarpine and Physostigmine. The method applied for these experiments was similar to the above-described Hypobare-Hypoxia model. Groups of mice were treated orally with an aqueous suspension of the extract (or with water). Pilocarpine and Physostigmine, respectively (or water) were administered 30 min later. The hypoxia tests were carried out 30 min after the second application. The results obtained are shown in Table XI.

Further tests showed that the "enriched" extract potentiates the analgetic activities of Pilocarpine and Physostigmine, but does not influence the effects of cholinomimetics (Oxotremorine) producing hypothermia, tremor and salivation. The analgesia tests were carried out according to the hotplate test (J. Pharm. Pharmacol., 9, 381, 1957) and the tests for hypothermia, tremor and salivation according to the method described by Gouret (J. Pharmacol., 4, 105–128, 1973). Subsequently, the mice were treated with extract and Physostigmine etc., in a manner similar to the method described above in connection with the hypoxia tests. The results obtained are shown in Tables XII and XIII.

TABLE XI
Influence of the bilobalide-containing extract from Ginkgo biloba on the anti-hypoxic effects of Pilocarpine and Physostigmine

| Treatment | Dose (mg/kg) | Survival time in sec (M ± SEM) treated animals | Survival time in sec (M ± SEM) control animals | % effect |
|---|---|---|---|---|
| extract | 50 (p.o.) | 73.7 ± 7.60 | 84.4 ± 4.40 | — |
| Physostigmine | 0.2 (i.p.) | 190.63 ± 26.2 | 80.6 ± 9.64 | 20 |
| extract + Physostigmine | 50 (p.o.) + 0.2 (i.p.) | 354.4 ± 22.6 | 103.1 ± 15.18 | 80 |
| Pilocarpine | 2 (i.p.) | 178.6 ± 24.8 | 86.7 ± 6.82 | 30 |
| extract + Pilocarpine | 50 (p.o.) + 2 (i.p.) | 382.6 ± 46.4 | 92.4 ± 13.64 | 90 |

TABLE XII
Influence of the bilobalide-containing extract from Ginkgo biloba on the analgetic effects of Physostigmine and Pilocarpine

| Test No. | Treatment | Dose (mg/kg) | Latent period (sec) (M ± SD) | % effect A |
|---|---|---|---|---|
| 1 | control | — | 14.5 ± 3.48 | 0 |
| | extract | 200 (p.o.) | 14.4 ± 4.56 | 0 |
| | Physostigmine | 0.1 (s.c.) | 31.1 ± 13.9 | 10 |
| | extract + Physostigmine | 200 (p.o.) + 0.1 (s.c.) | 55.84 ± 9.74 | 80 |
| | Physostigmine | 0.2 (s.c.) | 44.1 ± 17.69 | 50 |
| | extract + Physostigmine | 200 (p.o.) + 0.2 (s.c.) | 50.7 ± 13.04 | 80 |
| 2 | control | — | 15.74 ± 3.47 | 0 |
| | Pilocarpine | 5 (s.c.) | 24.9 ± 13.32 | 10 |
| | extract + Pilocarpine | 200 (p.o.) + 5 (s.c.) | 50.68 ± 13.04 | 60 |

A The percentage of animals having a latent period of more than 60 sec.

TABLE XIII
Influence of the bilobalide-containing extract from Ginkgo biloba on Oxotremorine, induced hypothermia, tremor and salivation

| Treatment | Dose (mg/kg) | Hypothermia (°C.) (M ± SD) | Tremor % | Salivation % |
|---|---|---|---|---|
| control | — | −0.24 ± 0.18 | 0 | 0 |
| extract | 200 (p.o.) | 0.18 ± 0.28 | 0 | 0 |
| Oxotremorine | 0.1 (i.p.) | 2.5 ± 0.82 | 0 | 60 |
| extract + Oxotremorine | 200 (p.o.) + 0.1 (i.p.) | 2.6 ± 0.96 | 0 | 50 |
| Oxotremorine | 0.2 (i.p.) | 5.23 ± 1.19 | 50 | 100 |
| extract + Oxotremorine | 200 (p.o.) + 0.2 (i.p.) | 4.92 ± 1.28 | 50 | 100 |

It is known to apply Physostigmine and other cholinomimetics for the therapy of various diseases. The narrow therapeutical scope of these substances restricts their use. The most important side effects complicating a therapy with cholinomimetics are tremor, salivation and hypothermia. The findings that the "enriched"

extract only potentiates the useful effects of the cholinomimetics and not the side effects of these medicaments shows that an additional therapy with the extract would enlarge the therapeutical scope of the cholinomimetics, thus offering the patients a useful therapy.

Bilobalide can be administered in the form of customary medicaments, for example ointments, solutions, coated tablets, tablets, capsules or solutions for injection or infusion, orally or parenterally, for example intramuscularly or intravenously, or topically, for example in the form of plasters acting percutaneously. The dose depends on the severity of the disease and the weight of the patient. Coated tablets can be administered after the meals in the morning and evening. The daily doses administered are 5 to 40 mg bilobalide with the normal drug forms, 0.5 to 5 mg bilobalide on parenteral administration, and 5 to 100 mg bilobalide on cutaneous administration.

Bilobalide can be isolated from the leaves of Ginkgo biloba by, for example, the method indicated by K. Weinges and W. Bähr, Justus Liebigs Ann. Chem., 724 (1969), 214–216.

It is possible to use the customary vehicles and additives for the preparation of medicaments containing bilobalide. Examples of customary vehicles are water, physiological saline, alcohols, polyethylene glycols, glycerol esters, gelatin, carbohydrates, such as lactose and starch, magnesium stearate and talc. Examples of customary additives are preservatives, sterilising agents, lubricants, wetting agents and emulsifiers, colorants, masking flavours and aromatic substances. The selection of the vehicles and additives depends on whether the formulations according to the invention are to be administered enterally, parenterally or locally.

1. TABLETS CONTAINING PURE BILOBALIDE

To prepare tablets each weighing 100 mg and containing 5 mg bilobalide, the following are necessary 5 g bilobalide
58.5 g lactose
18 g microcrystalline cellulose
18 g maize starch
0.5 g magnesium stearate The first four ingredients are mixed, granulated and, after addition of magnesium stearate, compressed to form tablets in a tabletting machine.

2. TABLETS WHICH CONTAIN GINKGO EXTRACT CONTAINING BILOBALIDE

The following recipe results when an extract of ginkgo enriched in bilobalide is used:

| n g | ginkgo extract, corresponding to 5 mg bilobalide |
| --- | --- |
| (200-n) g | lactose |
| 25 g | microcrystalline cellulose |
| 24 g | maize starch |
| 1 g | magnesium stearate |

The first four ingredients are mixed, granulated and, after addition of magnesium stearate, compressed in a tabletting machine to give tablets each weighing 250 mg.

3. CAPSULES

| 7 g | bilobalide |
| --- | --- |
| 75 g | lactose |
| 20 g | maize starch |

The ingredients are mixed homogeneously and processed in a customary manner to give capsules containing 100 mg.

4. INJECTION AMPOULES

To prepare injection ampoules each containing 2 ml, which contain 0.5 mg bilobalide, the following are required

| 0.25 g | bilobalide |
| --- | --- |
| 9 g | sodium chloride |
| ad 100 g | double-distilled water |

The first two ingredients are dissolved in water with gentle heating and stirring. The solution is sterilised by filtration and dispensed into 2 ml ampoules.

5. LIQUID ORAL DRUG FORM

| 5 g | bilobalide |
| --- | --- |
| 10 g | aromatic essence |
| 5 g | sodium saccharinate |
| 400 g | ethyl alcohol |
| 580 g | distilled water or deionised water. |

The first three ingredients are dissolved in the mixture of ethanol and water. The resulting solution is dispensed into 100 ml bottles. The single dose is 1 ml.

6. OINTMENT

| 0.5 g | bilobalide |
| --- | --- |
| 30 g | emulsifying cetylstearyl alcohol |
| 35 g | high viscosity paraffin |
| 34.5 g | white vaseline. |

The mixture of cetylstearyl alcohol, white vaseline and high viscosity paraffin is melted. The bilobalide is then stirred in. The dosage is 1 to 10 g of ointment per treatment.

What is claimed is:

1. A pharmaceutical composition useful for the treatment of neuropathic disorders which comprises a combination of flavone glycosides and bilobalide in a pharmaceutical carrier wherein the concentration of bilobalide and flavone glycosides are cooperatively sufficient to alleviate neuropathic disorders.

2. The pharmaceutical composition according to claim 1 which is a whole extract of the leaves of ginkgo bilboa, the extract containing flavone glycosides and bilobalide in amounts cooperatively sufficient to alleviate neuropathic disorders.

3. The pharmaceutical composition according to claim 1 wherein the content of bilbobalide is from 0.5 to 10 mg and the Ginko biloba monoextract content is 25 mg. to 100 mg.

4. The pharmaceutical composition according to claim 3 wherein the content of bilobalide is from about 0.5% to about 40% and residual monoextract of Ginko biloba from 99.5% to 60%.

5. The pharmaceutical composition according to claim 3 wherein the content of bilobalide is from about 3% to about 20% and residual monoextract of Ginkgo biloba from 97% to 80%.

6. The pharmaceutical composition according to claim 1 wherein the neuropathic disorders are demyelinating neuropathies, encephalopathies and myelopathies or cerebral oedemas.

7. The pharmaceutical composition according to claim 2 wherein the neuropathic disorders are demyelinating neuropathies, encephalopathies and myelopathies or cerebral oedemas.

* * * * *